Dec. 2, 1958 H. C. SWIM Plant Pat. 1,775
ROSE PLANT
Filed Jan. 3, 1958
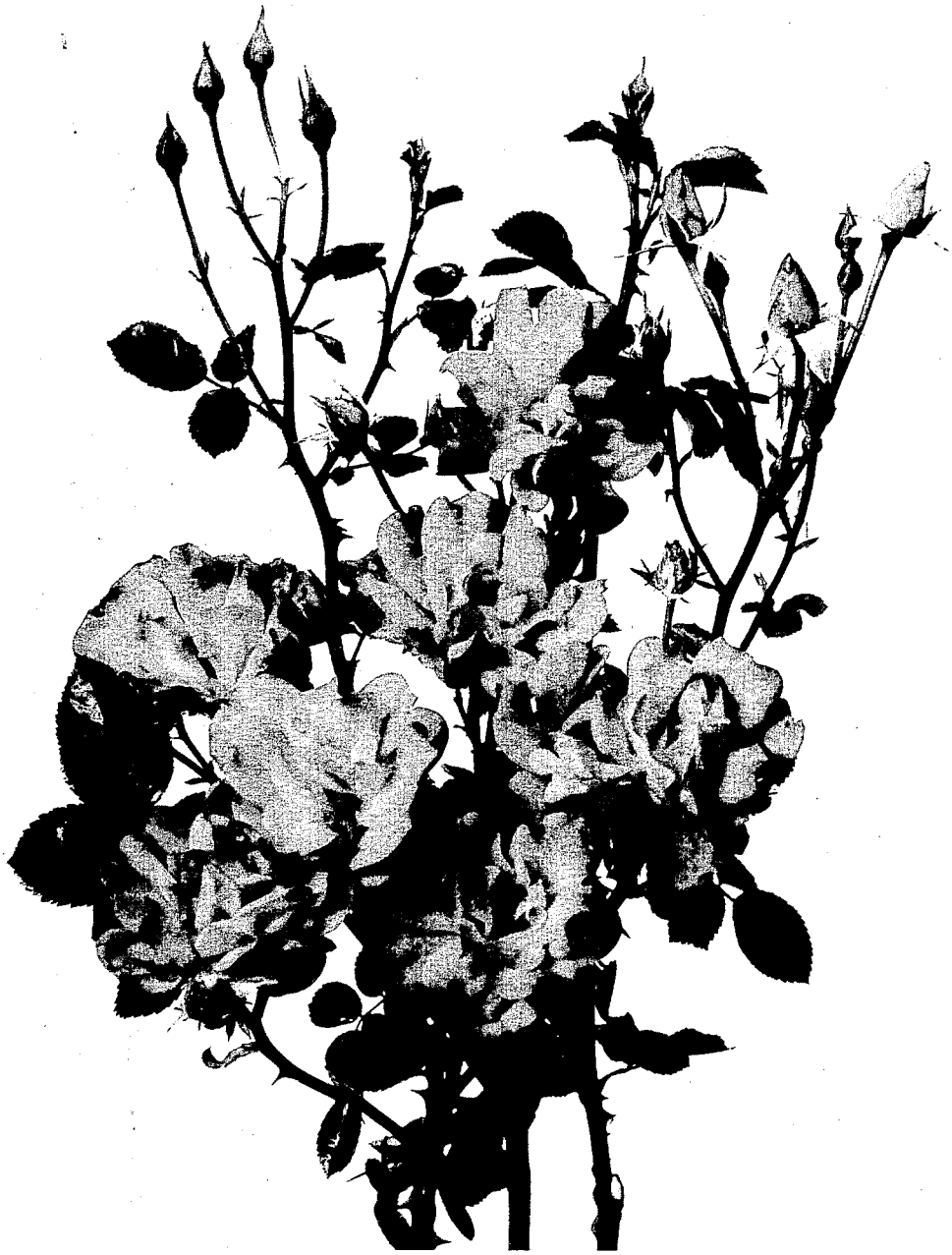
Inventor
H. C. Swim
By: Robb & Robb
Attorneys.

United States Patent Office

Plant Pat. 1,775
Patented Dec. 2, 1958

1,775

ROSE PLANT

Herbert C. Swim, Ontario, Calif., assignor to Armstrong Nurseries, Inc., Ontario, Calif., a corporation of California Application January 3, 1958, Serial No. 707,071

1 Claim. (Cl. 47—61)

The present invention relates to a new and distinct variety of rose plant of the floribunda class, which was originated by me by crossing the variety "World's Fair" (Plant Patent No. 362) with the variety "Pinocchio" (Plant Patent No. 484), and has for its primary objective the production of a new variety which combines the most desirable characteristics of the two parent varieties. This objective was fully achieved by employing "World's Fair" as the seed patent, and "Pinocchio" as the pollen parent.

As the result of the aforementioned breeding, I have produced a new rose variety which in definitely differentiated from its parents, as well as from all other varieties of which I am aware, as evidenced by the following unique combination of predominant features:

(1) Bushy medium sized, vigorous and very floriferous habits of plant growth;

(2) The habit of bearing its flowers in many clusters of medium size;

(3) Double flowers of medium size;

(4) An attractive, high-centered, loose, informal, open-flower form, with the centers of the flowers showing; and (5) A bright red flower color which is relatively unfading.

In comparison with its seed parent, "World's Fair," the flowers of the new variety are substantially smaller in size than those of this parent, but the plant is much more floriferous and has more flowers in each cluster.

As compared with its pollen parent, "Pinocchio," the flowers of my new variety have substantially fewer petals (usually from 18 to 20), the flowers are fewer in number per cluster, while the color of the flowers is red and quite different from the color of the flowers of this parent, which may be best described as pink, suffused with salmon.

Asexual reproduction of the new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilsons' Horticultural Colour Chart (hereinafter abbreviated as "Wilson") and Robert Ridgway's Color Standards and Nomenclature (hereinafter abbreviated as "Ridgway"), as indicated:

Class: Floribunda.
Breeding: Seedling.
*Seed parent.*—"World's Fair."
*Pollen parent.*—"Pinocchio."
Propagation: Holds its distinguishing characteristics through succeeding propagations by budding.

*Flower*

Locality where grown and observed: Ontario, California.
Flowers borne: Usually from 3 to 5 or more per stem; in regular, somewhat flat clusters; on normal stems of from short to medium length.
Quantity of bloom: Very abundant.
Continuity: Nearly continuous during growing season.
Fragrance: Slight.
Bud:
*Peduncle.*—Average length; from slender to average caliper; erect; moderately smooth; some stipitate glands; few prickles. Color—near Javel Green, Plate V (Ridgway), overlaid with near Tawny, Plate XV (Ridgway).
*Before calyx breaks.*—Size—small. Form—short; ovoid; usually with slender, bristle-like foliaceous parts extending beyond the tip of the bud equal to ¼ or more of its length.
*As calyx breaks.*—Color—near Indian Lake, Plate 826, page 170 (Wilson).
*Sepals.*—Permanent; medium length; recurved. Color: inside—near Light Grape Green, Plate XLI (Ridgway); outside—between Absinthe Green, Plate XXXI (Ridgway) and Rainette Green, Plate XXXI (Ridgway). Inner surface—lined with fine, woolly tomentum; margins of alternate sepals lined with fine, woolly tomentum, and others lined with stipitate glands and slender, bristle-like foliaceous parts. Outer surface—lined with few stipitate glands and occasional hairs.
*As first petal opens.*—Size—small. Form—short; from ovoid to urn-shaped. Color: outside—near Indian Lake, Plate 826/1, page 170 (Wilson), with point of attachment near Empire Yellow, Plate 603, page 66 (Wilson); inside—between Cardinal Red, Plate 822, page 168 (Wilson) and Chrysanthemum Crimson, Plate 824, page 169 (Wilson).
*Opening.*—Opens up well; is not retarded from opening by cold, hot, wet or dry weather.
Bloom:
*Size (when fully open).*—From small to average; usually from 2½ inches to 3 inches.
*Petalage.*—Double; usually from about 18–20 petals, plus from 2–4 petaloids; arranged regularly.
*Form.*—High-centered at first, but becoming from cupped to high-centered; petals at first being very loosely cupped, with tips reflexed somewhat outward and becoming later at maturity more loosely flat-cupped, with tips and lateral margins reflexed slightly outward.
Petals:
*Texture.*—Medium thickness; leathery. Inside—slightly velvety. Outside—from shiny to satiny.
*Shape.*—Outside—broadly obovate, with apex flat and sometimes with one or two notches. Intermediate—broadly obovate, with apex from rounded to flat, with one or two notches. Inside—broadly obovate; irregular margin; apex from rounded to flat, and with one or two notches.

This description of a newly opened flower was made from a rose grown outdoors in the month of October, at Ontario, California:

*Color.*—Outer petal: outside surface—between Cardinal Red, Plate 822/2, page 168 (Wilson) and Cardinal Red, Plate 822/3, page 168 (Wilson), with base at point of attachment near Empire Yellow, Plate 603/1, page 66 (Wilson); inside surface—between Cardinal Red, Plate 822, page 168 (Wilson) and Currant Red, Plate 821, page 167

(Wilson), with point of attachment near Empire Yellow, Plate 603, page 66 (Wilson). Intermediate petal: outside surface—near Cardinal Red, Plate 822/3, page 168 (Wilson), with point of atchment near Empire Yellow, Plate 603/1, page 66 (Wilson); inside surface—between Currant Red, Plate 821, page 167 (Wilson) and Cardinal Red, Plate 822, page 168 (Wilson), with point of attachment near Empire Yellow, Plate 603, page 66 (Wilson). Inner petal: outside surface—near Cardinal Red, Plate 822/3, page 168 (Wilson), with point of attachment near Empire Yellow, Plate 603/1, page 66 (Wilson); inside surface—near Cardinal Red, Plate 822/1, page 168 (Wilson), with point of attachment near Empire Yellow, Plate 603, page 66 (Wilson).

This description was made from a rose that was open for 3 days outdoors in the month of October, at Ontario, California:

*Color.*—Outer petal: outside surface—near Cardinal Red, Plate 822/3, page 168 (Wilson), with point of attachment near Empire Yellow, Plate 603/3, page 66 (Wilson); inside surface—near Cardinal Red, Plate 822/1, page 168 (Wilson), with point of attachment near Empire Yellow, Plate 603/3, page 66 (Wilson). Inner petal: outside surface—near Cardinal Red, Plate 822/3, page 168 (Wilson), with point of attachment near Empire Yellow, Plate 603/3, page 66 (Wilson); inside surface—near Cardinal Red, Plate 822/1, page 168 (Wilson), with point of attachment near Empire Yellow, Plate 603/3, page 66 (Wilson).

*General color effect.*—Newly opened flower—between Cardinal Red, Plate 822, page 168 (Wilson) and Cardinal Red, Plate 822/1, page 168 (Wilson), with point of attachhment near Empire Yellow, Plate 603/3, page 66 (Wilson). 3-days open—near Cardinal Red, Plate 822/1, page 168 (Wilson), with point of attachment near Empire Yellow, Plate 603/3, page 66 (Wilson).

*Flower longevity.*—On bush in garden—from 3 to 5 days in October. Cut roses grown outdoors and kept at living-room temperatures—from 4 to 5 days in October.

*Behaviour.*—Petals drop off cleanly.

*Reproductive organs*

Stamens: Many; arranged regularly about pistils.

Filaments: From 4 to 8 mm. in length; most with anthers. Color—near Chinese Yellow, Plate 606, page 68 (Wilson).

Anthers: Medium size; all open approximately at once. Color: upper side—margins near Indian Yellow, Plate 6, page 6 (Wilson), with remainder near Saturn Red, Plate 13/2, page 13 (Wilson); under side—margins near Indian Yellow, Plate 6, page 6 (Wilson), with remainder near Saturn Red, Plate 13/2, page 13 (Wilson).

Pollen: From moderate to abundant. Color—near Indian Yellow, Plate 6/1, page 6 (Wilson).

Pistils: Few; usually about 30 in number.

Styles: Moderately even; from 6 to 8 mm. in length; from thin to average caliper; somewhat loosely bunched.

Stigma: Color—near Dresden Yellow, Plate 64/2, page 64 (Wilson).

Ovaries: Usually most enclosed in calyx, but some protruding from calyx.

Hips: Average length; globular; smooth; with walls thick and fleshy. Color (mature)—near Zinc Orange, Plate XV (Ridgway).

Seeds: Medium size; usually from 12 to 15 per hip when open pollinated.

*Plant*

Growth: Semi-spreading; much-branched; vigorous; with canes of medium caliper.

Foliage:

*Leaves.*—Compound of usually from 5 to 7 leaflets; from normal abundance to abundant; medium size; leathery; semi-glossy.

*Leaflets.*—Shape—usually ovate, with apex acute; round base; margin usually doubly serrate. Color—mature: upper surface—near dark Dull Yellow-Green, Plate XXXII (Ridgway); under surface—near Stone Green, Plate XLII (Ridgway); young: upper surface—between Olive Brown, Plate XL (Ridgway) and Dark Vinaceous-Drab, Plate XLV (Ridgway); under surface—between Citrine-Drab, Plate XL (Ridgway) and Vinaceous-Drab, Plate XLV (Ridgway).

*Rachis (the supporting stem of the compound leaf).*—Average size. Upper side—grooved; hairy; some stipitate glands on edges of groove. Under side—smooth; with stipitate glands and from 2 to 3 prickles.

*Stipules.*—Medium length; medium width; with medium length points turning out at an angle of less than 45°.

Main stems:

*Color.*—Near Asphodel Green, Plate XLI (Ridgway).

*Large prickles.*—Several; medium length; almost straight; with medium length, narrow base. Color—near Sayal Brown, Plate XXIX (Ridgway).

*Small prickles.*—Few. Color—near Sayal Brown, Plate XXIX (Ridgway).

*Hairs.*—None.

Branches:

*Color.*—Near Light Elm Green, Plate XVII (Ridgway).

*Large prickles.*—Several; medium length; almost straight or hooked slightly downward; with medium length, narrow base. Color—near Sayal Brown, Plate XXIX (Ridgway).

*Small prickles.*—Very few. Color—near Sayal Brown, Plate XXIX (Ridgway).

*Hairs.*—None.

New shoots:

*Color.*—Near Benzo Brown, Plate XLVI (Ridgway).

*Large prickles.*—Several; medium length; almost straight or hooked slightly downward; with medium length, narrow base. Color—near Ochre Red, Plate XXVII (Ridgway).

*Small prickles.*—Few. Color—near Ochre Red, Plate XXVII (Ridgway).

*Hairs.*—None.

I claim:

A new and distinct variety of rose plant of the floribunda class, substantially as herein shown and described, characterized particularly as to novelty by its bushy, medium-sized, vigorous and very floriferous habits of growth, its habit of bearing flowers in clusters of medium size, its double flowers of medium size, the showy, high-centered, loose, informal and open-flower form of its flowers which have their centers exposed, and the bright and relatively unfading red general color tonality of its flowers.

No references cited.